United States Patent [19]

Cragoe, Jr. et al.

[11] 4,006,180
[45] Feb. 1, 1977

[54] [1,3-DIHYDROXY-2-SUBSTITUTED AND 2,2-DISUBSTITUTED-INDANYLOXY(OR THIO)]ALKANOIC ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[22] Filed: July 31, 1974

[21] Appl. No.: 492,943

Related U.S. Application Data

[63] Continuation-in-part of Ser. No. 405,964, Oct. 12, 1973, abandoned.

[52] U.S. Cl. .............. 260/473 F; 260/308 D; 260/332.2 A; 260/332.3 R; 260/465 F; 260/470; 260/501.1; 260/516; 260/520 C; 260/559 B; 260/623 R
[51] Int. Cl.² ........................................ C07C 69/76
[58] Field of Search .............. 260/473 F, 520

[56] References Cited

UNITED STATES PATENTS

| | | | |
|---|---|---|---|
| 3,369,025 | 2/1968 | Bolhofer | 260/520 |
| 3,668,241 | 6/1972 | Cragoe et al. | 260/520 |
| 3,704,314 | 11/1972 | Cragoe et al. | 260/520 |
| 3,776,944 | 12/1973 | Brown et al. | 260/520 |
| 3,906,032 | 9/1975 | Hauck | 260/473 F |

OTHER PUBLICATIONS

Topless et al, J. Pharm. Sci. 57 (5) p. 737 (1968).

*Primary Examiner*—Paul J. Killos
*Attorney, Agent, or Firm*—Michael C. Sudol, Jr.; J. Jerome Behan; Rudolph J. Anderson

[57] ABSTRACT

[1,3-Dihydroxy-2-substituted and 2,2-disubstituted-indanyloxy(or thio)]alkanoic acids and their salts, esters and amides are disclosed. The products display a dual pharmaceutical utility in that they exhibit diuretic, saluretic and uricosuric activity. The acid products are prepared by treating a 1,3-dioxo-2-substituted or 2,2-disubstituted-indanyloxy(or thio)alkanoic acid with a reducing agent.

16 Claims, No Drawings

[1,3-DIHYDROXY-2-SUBSTITUTED AND 2,2-DISUBSTITUTED-INDANYLOXY(OR THIO)]ALKANOIC ACIDS

This application is a continuation-in-part of our co-pending application Ser. No. 405,964, filed Oct. 12, 1973, now abandoned.

This invention relates to a new class of chemical compounds which can be described generally as [1,3-dihydroxy-2-substituted and 2,2-disubstituted-indanyloxy(or thio)]alkanoic acids and to the non-toxic, pharmacologically acceptable salt, ester and amide derivatives. It is also an object of this invention to describe a method for the preparation of the [1,3-dihydroxy-2-substituted and 2,2-disubstituted-indanyloxy/or thio)]alkanoic acids. Pharmacological studies show that the instant products are effective diuretic and saluretic agents which can be used in the treatment of conditions associated with electrolyte and fluid retention. The instant products are also useful in the treatment of hypertension. In addition, these compounds are able to maintain the uric acid concentration in the body at pretreatment levels or to even effect a decrease in the uric acid concentration.

When administered in therapeutic dosages, in conventional vehicles, the instant products effectively reduce the amount of sodium and chloride ions in the body, lower dangerous excesses of fluid levels to acceptable levels and, in general, alleviate conditions usually associated with edema. In addition, these compounds overcome a major problem associated with many of the presently available diuretics and saluretics. Many of the presently available diuretics and saluretics have a tendency upon administration to induce hyperuricemia which may result in the precipitation of uric acid or sodium urate, or both, in the body which may cause from mild to severe gout. The instant compounds of this invention now provide an effective tool to treat those patients requiring diuretic an saluretic treatment without incurring the risk of inducing gout.

[1,3-Dihydroxy-2-substituted and 2,2-disubstituted-indanyloxy(or thio)]alkanoic acids of the invention have the following structural formula:

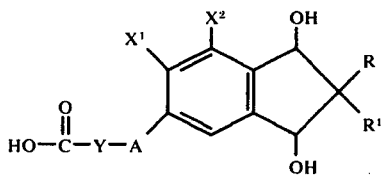

wherein A is oxygen or sulfur; R is lower alkyl containing from 1 to 5 carbon atoms such as methyl, ethyl, n-propyl, isopropyl, n-butyl, isobutyl, tert-butyl, n-pentyl and the like; cycloalkyl, for example, cycloalkyl containing from 5 to 6 nuclear carbon atoms such as cyclopentyl, cyclohexyl and the like, aryl such as phenyl and substituted aryl wherein the substituent is lower alkyl or halo; thienyl and substituted thienyl wherein the substituent is lower alkyl or halo; $R^1$ is hydrogen, lower alkyl containing from 1 to 5 carbon atoms such as methyl, ethyl, n-propyl, isopropyl, n-butyl, isobutyl, tert-butyl, n-pentyl and the like, lower alkenyl containing from 3 to 5 carbon atoms such as allyl, 1-, 2- or 3-butenyl, 1-, 2-, 3- or 4-pentenyl and the like, lower alkynyl containing from 3 to 5 carbon atoms such as propargyl, 1-, 2- or 3-butynyl, 1-, 2-, 3- or 4-pentynyl and the like, phenyl lower alkyl wherein the lower alkyl contains from 1 to 3 carbon atoms such as benzyl, phenethyl, phenylpropyl and the like, phenyl lower alkenyl wherein the lower alkenyl contains from 2 to 5 carbon atoms such as cinnamyl and the like, aryl or substituted aryl such as loweralkylaryl or haloaryl; thienyl or subsitutited thienyl such as loweralkylthienyl or halothienyl, or R and $R^1$ may be joined together with the carbon atoms to which they are attached to form a cycloalkyl radical containing from 3 to 7 nuclear carbon atoms, for example, cyclopropyl, cyclobutyl, cyclopentyl, cyclohexyl, cycloheptyl and the like; $X^1$ is hydrogen, methyl or halo such as chloro, bromo, fluoro and the like; and $X^2$ is methyl or halo such as chloro, bromo, fluoro and the like; or $X^1$ and $X^2$ may be joined to form a hydrocarbylene chain containing from 3 to 4 carbon atoms, for example, trimethylene, tetramethylene, 1,3-butadienylene and the like, and Y is an alkylene or haloalkylene radical having a maximum of 4 carbon atoms which contain from 1 to 3 linear carbon atoms between the oxy (or thio) and carboxy group, for example, methylene, ethylidene, propylidene, isopropylidene, ethylene, trimethylene, fluoromethylene and the like, and the non-toxic pharmaceutically acceptable salt, ester and amide derivatives thereof.

The preferred embodiments of this invention are the [1,3-dihydroxy-2-substituted and 2,2-disubstituted-indanyloxy]alkanoic acids having the following structural formula:

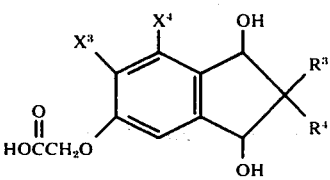

wherein $R^3$ is lower alkyl containing from 1 to 3 carbon atoms such as methyl, ethyl, n-propyl or cycloalkyl containing 5 or 6 nuclear carbon atoms such as cyclopentyl or cyclohexyl, and $R^4$ is hydrogen, lower alkyl containing from 1 to 3 carbon atoms such as methyl, ethyl, n-propyl or isopropyl, aryl such as phenyl or substituted phenyl such as lower alkylphenyl wherein the lower alkyl contains from 1 to 3 carbon atoms such as methyl, ethyl, n-propyl or isopropyl such as tolyl; halophenyl such as chlorophenyl; thienyl, lower alkylthienyl wherein the lower alkyl contains from 1 to 3 carbon atoms such as methyl, ethyl, n-propyl or isopropyl, halothienyl; or $R^3$ and $R^4$ may be joined together with the carbon atoms to which they are attached to form a cyclohexyl and the like, and $X^3$ and $X^4$ are the same or different radicals selected from methyl or chloro; and the non-toxic, pharmacologically acceptable salt, ester and amide derivatives. The foregoing class of compounds exhibits particularly good diuretic and saluretic activity and also either maintains the uric acid concentration in the body at pretreatment levels or even causes a decrease in the uric acid concentration.

A further more preferred embodiment of this invention are the [1,3-dihydroxy-2-substituted and 2,2-disubstituted-indanyloxy]alkanoic acids having the formula:

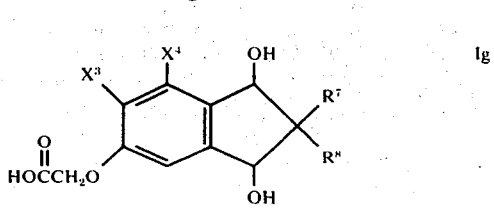

wherein $R^7$ is lower alkyl containing from 1 to 3 carbon atoms such as methyl, ethyl, n-propyl or isopropyl; $R^8$ is hydrogen, lower alkyl containing from 1 to 3 carbon atoms such as methyl, ethyl, n-propyl, isopropyl, phenyl, p-chlorophenyl or thienyl; and $X^3$ and $X^4$ are the same or different radicals selected from methyl or chloro; and the non-toxic pharmaceutically acceptable salt and ester derivatives thereof.

The foregoing especially preferred class of compounds also exhibits particularly good diuretic and saluretic activity and also either maintains the uric acid concentration in the body at pretreatment levels or even causes a decrease in the uric acid concentration.

The [1,3-dihydroxy-2-substituted and 2,2-disubstituted-indanyloxy(or thio)]alkanoic acids can be prepared as exemplified by the following equations:

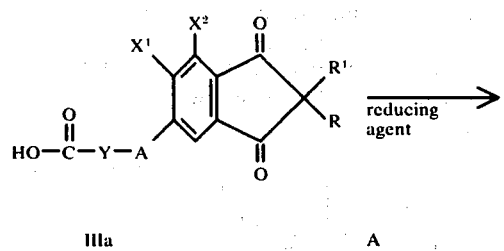

wherein R, $R^1$, $X^1$, $X^2$, A and Y are as previously defined.

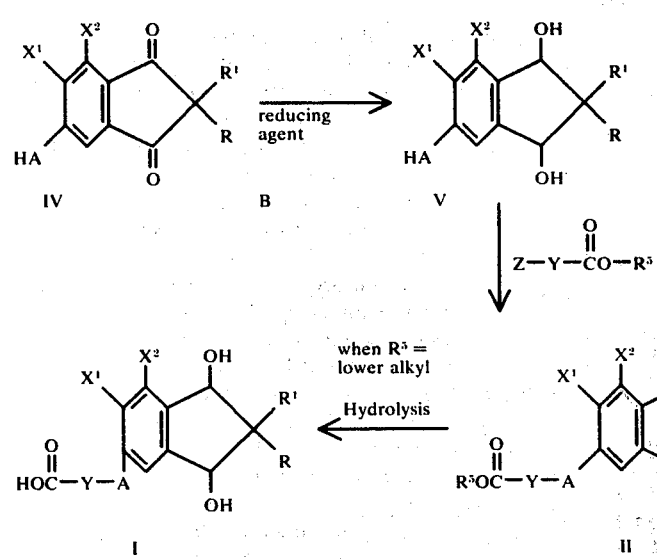

wherein R, $R^1$, $X^1$, $X^2$, A and Y are as defined above and $R^5$ is hydrogen or lower alkyl and Z is halo.

Generally for the preparation shown in Scheme A above, a [1,3-dioxo-2-substituted-indanyloxy(or thio)-]alkanoic acid is reduced with a reducing agent, generally an alkali metal reducing agent such as potassium borohydride in water or sodium borohydride to yield Compound I in reaction Scheme A. Generally this reaction can be run at anywhere from 0°–50° C. but preferably at room temperature. A 2:1 mole ratio of the reducing agent to the starting material III is used. The product I can be isolated by acidifying the reaction mixture with any mineral acid such as dilute hydrochloric acid which will precipitate the product from solution. The product can then be isolated by filtering the reaction mixture.

Another process for preparing the diol end product I is shown in reaction Scheme B. In this reaction, 5-hydroxy(or mercapto)-1,3-indanedione (IV) is reduced to yield the 1,3 diol intermediate (V) which compound is then reacted with a lower alkyl halo ester or acid to yield the desired product (I) or an ester thereof (II). If an ester (II) is formed, a further hydrolysis step which anyone skilled in the art can perform yields the desired product (I).

The first part of reaction scheme B, namely, the reduction can be performed with a reducing agent such as lithium aluminum hydride or sodium bis-(2-methoxyethoxy)aluminum hydride. The reaction is carried out in an inert solvent such as tetrahydrofuran, ether or benzene. The reaction is run at anywhere from 0°–50° C.; preferred temperature being about room temperature and for a time sufficient to complete the reaction, namely from about one-half to two hours, although the reaction is generally complete in about one-half hour. The intermediate product, 5-hydroxy(or mercapto)-1,3-indandiol (V) is then isolated from the organic phase by evaporating off the reaction solvent.

The second step of reaction Scheme B is the reaction with halo lower alkanoic acid ester or halo lower alkanoic acid. In general, this reaction is conducted in the presence of a base such as an alkali metal carbonate, hydroxide or alkoxide such as potassium carbonate, sodium carbonate, potassium hydroxide, sodium hydroxide, sodium ethoxide and the like. Any solvent which is inert or substantially inert to the reactants and in which the reagents are reasonably soluble may be employed. Acetone, ethanol and dimethylformamide, for example, have proved to be particularly advantageous solvents. The reaction may be conducted at a temperature in the range of from about 25° C. to the reflux temperature of the particular solvent employed. The reaction with the haloalkanoic acid or ester is generally complete in about 10 to 60 minutes. If the haloalkanoic acid ester is employed, the ester obtained may be hydrolyzed to the free acid by methods well known to those skilled in the art.

Briefly the preparation of the starting materials can be depicted as follows:

In general, the reaction is conducted in the presence of a base such as an alkali metal carbonate, hydroxide or alkoxide such as potassium carbonate, sodium carbonate, potassium hydroxide, sodium hydroxide, sodium ethoxide and the like. Any solvent which is inert or substantially inert to the reactants and in which the reagents are reasonably soluble may be employed. Acetone, ethanol and dimethylformamide, for example, have proved to be particularly advantageous solvents. The reaction may be conducted at a temperature in the range of from about 25° C. to the reflux temperature of the particular solvent employed. The reaction with the alkylating agent is generally complete in about 10 to 60 minutes.

Still another method for preparing a 2,2-disubstituted-6-lower alkoxy-1,3-indanedione (VIII above) is effected by treating the corresponding 2-substituted compound VII with a suitable arylating agent such as diaryliodonium halide, e.g. diphenyliodonium chloride or di-(substituted phenyl)iodonium halide, e.g. ditolyliodonium chloride or di-(p-chlorophenyl)iodonium

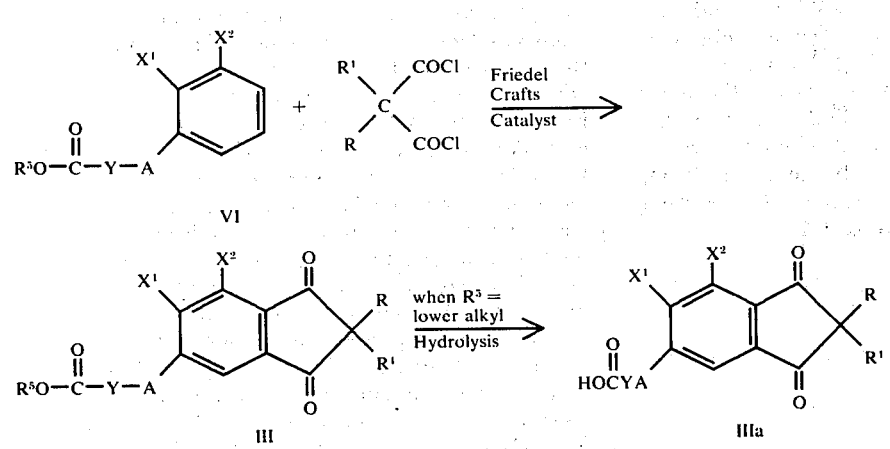

Another method for preparing a 2,2-disubstituted-6-lower alkoxy-1,3-indanedione (VIII, infra) consists of alkylating a 2-monosubstituted-6-lower alkoxy-1,3-indanedione (VII, infra) with an alkylating agent $R^2Z$ wherein $R^2$ is lower alkyl containing from 1 to 5 carbon atoms such as methyl, ethyl, n-propyl, isopropyl, n-butyl, isobutyl, tertbutyl, n-pentyl and the like, lower alkenyl containing from 3 to 5 carbon atoms such as allyl, 1-, 2- or 3-butenyl, 1-, 2-, 3- or 4-pentenyl and the like, lower alkynyl containing from 3 to 5 carbon atoms such as propargyl, 1-, 2- or 3-butynyl, 1-, 2-, 3- or 4-pentynyl and the like, phenyl lower alkyl wherein the lower alkyl contains from 1 to 3 carbon atoms such as benzyl, phenethyl, phenylpropyl and the like, phenyl lower alkenyl wherein the lower alkenyl contains from 2 to 5 carbon atoms such as cinnamyl and the like, and R, $X^1$, $X^2$ and Z are as defined above, and $R^6$ is lower alkyl.

The following equation illustrates this process:

chloride. Likewise dithienyliodonium halide is used to introduce the thienyl group into the 2-position of 2-substituted indandione.

This reaction is conducted by first treating the 2-substituted compound VII with a suitable base for example an alkali metal hydride such as sodium hydride and the like, an alkali metal alkoxide for example sodium ethoxide, potassium tertiary butoxide and the like; or an alkali metal amide such as sodium amide, lithium amide and the like. The resulting carbanion is then treated with the arylating agent. Any solvent which is inert or substantially inert to the reactants employed may be used; suitable solvents include for example 1,2-dimethoxyethane tertiary butanol, benzene, dimethylformamide and the like. The reaction may be conducted at a temperature in the range of from about 25°–150° C. The following equation illustrates this process:

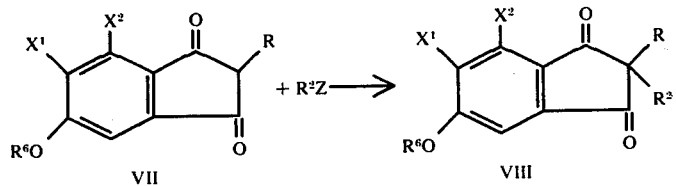

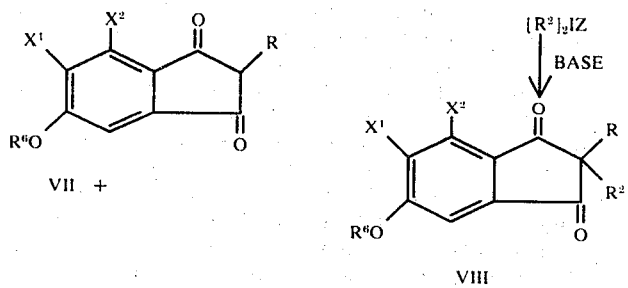

wherein all substituents are as defined above.

The 2-monosubstituted-6-lower alkoxy-1,3-indanedione (VII, supra) are prepared by reacting a phthalate ester (IX, infra) with a ketone, $(RCH_2)_2C=O$ in an inert solvent such as benzene, toluene, xylene and the like in the presence of a base such as sodium hydride, potassium tert-butoxide and the like at a temperature of from 50° to 150° C. but preferably at the refluxing temperature of the solvent employed. The following equation illustrates this process.

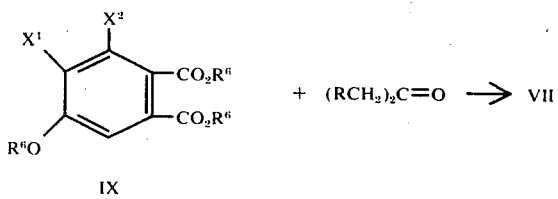

wherein R, $R^6$, $X^1$ and $X^2$ are as defined above.

The phthalic acids (IXa, infra) which are esterified by methods well known to those skilled in the art to give the phthalate esters (IX, supra), are prepared by the oxidation of a 2-substituted-5-lower alkoxy-1-indanone (X, infra) with an oxidizing agent such as potassium permanganate sodium dichromate or chromic acid and the like in a suitable solvent such as water or acetone and the like. The reaction is conducted at from 25° to 100° C. but preferably at the reflux temperature of the solvent employed. The following equation illustrates this process:

wherein R, $R^6$, $X^1$ and $X^2$ are as defined above with the exception that $X^1$ and $X^2$ is limited to halogen.

Also included within the scope of this invention are the ester and amide derivatives of the instant products which are prepared by conventional methods well known to those skilled in the art. Thus, for example, the ester derivative may be prepared by the reaction of a [1,3-dihydroxy-2-substituted and 2,2-disubstituted-indanyloxy(or thio)]alkanoic acid (I) of this invention with an alkyl halide in a suitable solvent such as dimethylformamide in the presence of a base such as potassium carbonate. The amide derivatives may be prepared by reacting the ester derivative (II) with ammonia, an appropriate mono-lower alkyl amine, di-lower alkyl amine or a hetero amine, such as piperidine, morpholine and the like, to produce the corresponding amide compound. These and other equivalent methods for the preparation of the ester and amide derivatives of the instant products will be apparent to one having ordinary skill in the art and to the extent that said derivatives are both non-toxic and physiologically acceptable to the body system, said derivatives are the functional equivalent of the corresponding [1,3-dihydroxy-2-substituted and 2,2-disubstituted-indanyloxy(or thio)]alkanoic acids.

In addition to the salts, esters and amides being functionally equivalent to the carboxylic products, those compounds wherein the carboxylic acid is replaced by a 5-tetrazolyl radical are also functionally equivalent to the carboxylic acids. These tetrazole analogs are prepared as depicted in the following equation:

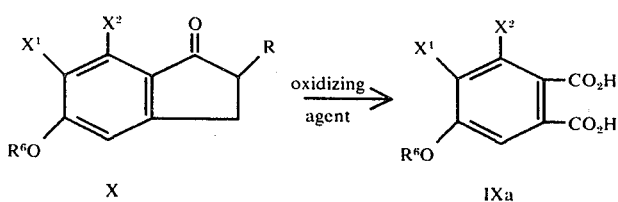

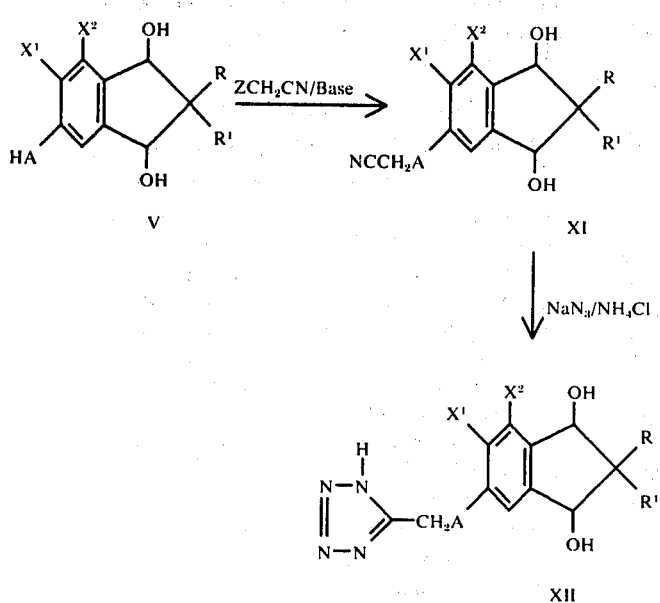

wherein A, R, R¹, X¹, X² and Z are as defined above.

The 2-substituted-6-hydroxy-indan-1,3-diol (V) is treated with a haloacetonitrile such as chloroacetonitrile, bromoacetonitrile or iodoacetonitrile in the presence of a base such as potassium carbonate and the like in a suitable solvent such as acetone, dimethylformamide, dimethoxyethane and the like at a temperature in the range of from 25° to 100° C. to afford the corresponding nitrile (XI, supra) which, upon treatment with sodium azide and ammonium chloride in dimethylformamide at a temperature in the range of from 25° to 100° C., affords the 5-(1,3-dihydroxy-2-substituted-6-indanyloxymethyl)tetrazole (XII, supra).

It is recognized that the instant [1,3-dihydroxy-2-substituted and 2,2-disubstituted-indanyloxy(or thio)]acetic acids all have chiral centers located at the 1 to 3 carbon atoms, and in some instances at the 2 carbon atom. The diasteromers that may form by the synthetic processes described can be separated by methods known to those skilled in the art, i.e., fractional crystallization, chromatography, etc. Likewise, optical isomers may be separated by known methods, i.e., fractional crystallization of salts formed from optically active bases or from esters or amides derived from optically active alcohols and amines.

This invention includes the diastereomeric mixtures and the pure enantiomers represented by each structure.

The following examples describe the preparation of specific compounds of this invention are meant to be illustrative only and not limiting to the scope of this invention.

EXAMPLE 1

(1,3-Dihydroxy-2-ethyl-4,5-dimethyl-6-indanyloxy)acetic acid

A stirred suspension of (1,3-dioxo-2-ethyl-4,5-dimethyl-6-indanyloxy)acetic acid (5.52 g., 0.02 mole) in water (200 ml.) is cooled to 5° C. and treated with a solution of potassium borohydride (4.0 g., 0.075 mole) in water (200 ml.) during a 1 hour period. The reaction is stirred for one hour then acidified with hydrochloric acid affording (1,3-dihydroxy-2-ethyl-4,5-dimethyl-6-indanyloxy)acetic acid.

EXAMPLE 2

[1',3'-dihydroxy-4'-chloro-5'-methylspiro(cyclopentane-1,2'-indan)-6'-yloxy]acetic acid Step A: 4'-Chloro-5'-methylspiro(cyclopentane 1,2'-indan)-1',3',6'-triol A solution of 4'-chloro-5'-methyl-6'-hydroxyspiro(-cyclopentane-1,2'-indan)-1',3'-dione (4.0 g., 0.015 mole) in tetrahydrofuran (100 ml.) is cooled to 15° C. and treated over 5 minutes with a solution of sodium bis-(2-methoxyethoxy)aluminum hydride (10 ml. of a 70% solution in benzene). The reaction is stirred one-half hour at 25° C., cooled to 10° C. and slowly treated with 20% aqueous hydrochloric acid until acidic. The organic phase is evaporated to an oil, dissolved in ether, washed with water, dried over magnesium sulfate and the solvent evaporated affording 4'-chloro-5'-methylspiro(cyclopentane-1,2'-indan)-1',3',6'-triol.

Step B: [1',3'-Dihydroxy-4'-chloro-5'-methylspiro(cyclopentane-1,2'-indan)-6'-yloxy]acetic acid A stirred mixture of 4'-chloro-5'-methylspiro(cyclopentane-1,2'-indan)-1',3',6'-triol (4.0 g., 0.015 mole), potassium carbonate (3.6 g.) and ethyl bromoacetate (3.1 ml.) in dimethylformamide (35 ml.) is heated at 55° C. for one-half hour in an inert atmosphere, treated with water (50 ml.) and 10N sodium hydroxide (5 ml.) then heated at 95° for one-half hour and poured into cold dilute hydrochloric acid affording [1',3'-dihydroxy-4'-chloro-5'-methylspiro(cyclopentane-1,2'-indan)-6'-yloxy]acetic acid.

EXAMPLE 3

(1,3-Dihydroxy-2-ethyl-2-phenyl-4,5-dichloro-6-indanyloxy)acetic acid

By the process of Example 2A but substituting for the 4'-chloro-5'-methyl-6'-hydroxyspiro(cyclopentane-1,2'-indan)- 1',3'-dione used therein an equivalent amount of 2-ethyl-2-phenyl-4,5-dichloro-6-hydroxyindan-1,3-dione there is obtained 2-ethyl-2-phenyl-4,5-dichloroindan-1,3,6-triol.

By the process of Example 2B but substituting for the 4'-chloro-5'-methylspiro(cyclopentane-1,2'-indan)1',3',6'-triol an equivalent amount of 2-ethyl-2-phenyl-4,5-dichloroindan-1,3,6-triol there is obtained (1,3-dihydroxy-2-ethyl-2-phenyl-4,5-dichloro-6-indanyloxy)acetic acid.

EXAMPLE 4

(1,3-Dihydroxy-2-methyl-2-ethyl-4,5-dichloro-6-indanyloxy)acetic acid

By the process of Example 2A, but substituting for the 4'-chloro-5'-methyl-6'-hydroxyspiro(cyclopentane-1,2'-indan)-1',3'-dione used therein an equivalent amount of 2-methyl-2-ethyl-4,5-dichloro-6-hydroxyindan-1,3-dione, there is obtained 2-methyl-2-ethyl-4,5-dichloroindan-1,3,6-triol.

By the process of Example 2B but substituting for the 4'-chloro-5'-methylspiro(cyclopentane-1,2'-indan)-1',3',6'-triol an equivalent amount of 2-methyl-2-ethyl-4,5-dichloroindan-1,3,6-triol, there is obtained (1,3-dihydroxy-2-methyl-2-ethyl-4,5-dichloro-6-indanyloxy)acetic acid.

EXAMPLE 5

(1,3-Dihydroxy-2,5-dimethyl-2-cyclopentyl-4-chloro-6-indanyloxy)acetic acid

By the process of Example 2A but substituting for the 4'-chloro-5'-methyl-6'-hydroxyspiro(cyclopentane-1,2'-indan)-1',3'-dione used therein an equivalent amount of 2,5-dimethyl-2-cyclopentyl-4-chloro-6-hydroxyindan-1,3-dione there is obtained 2,5-dimethyl-2-cyclopentyl-4-chloroindan-1,3,6-triol.

By the process of Example 2B but substituting for the 4'-chloro-5'-methylspiro(cyclopentane-1,2'-indan)-1',3',6'-triol an equivalent amount of 2,5-dimethyl-2-cyclopentyl-4-chloroindan-1,3,6-triol there is obtained (1,3-dihydroxy-2,5-dimethyl-2-cyclopentyl-4-chloro-6-indanyloxy)acetic acid.

EXAMPLE 6

(1,3-Dihydroxy-2-methyl-2-phenyl-4,5-dichloro-6-indanyloxy)acetic acid

By the process of Example 2A but substituting for the 4'-chloro-5'-methyl-6'-hydroxyspiro(cyclopentane-1,2'-indan)-1',3'-dione used therein an equivalent amount of 2-methyl-2-phenyl-4,5-dichloro-6-hydroxyindan-1,3-dione there is obtained 2-methyl-2-phenyl-4,5-dichloroindan-1,3,6-triol.

By the process of Example 2B but substituting for the 4'-chloro-5'-methylspiro(cyclopentane-1,2'-indan)-1',3',6'-triol an equivalent amount of 2-methyl-2-phenyl-4,5-dichloroindan-1,3,6-triol there is obtained (1,3-dihydroxy-2-methyl-2-phenyl-4,5-dichloro-6-indanyloxy)acetic acid.

EXAMPLE 7

[1,3-Dihydroxy-2-methyl-2-(p-chlorophenyl)-4,5-dichloro-6-indanyloxy]acetic acid By the process of Example 2A but substituting for the 4'-chloro-5'-methyl-6'hydroxyspiro(cyclopentane-1,2'-indan)-1',3'-dione used therein an equivalent amount of 2-methyl-2-(p-chlorophenyl)-4,5-dichloro-6-hydroxyindan-1,3-dione there is obtained 2-methyl-2-(p-chlorophenyl)-4,5-dichloroindan-1,3,6-triol.

By the process of Example 2B but substituting for the 4'-chloro-5'-methylspiro(cyclopentane-1,2'-indan)-1',3',6'-triol an equivalent amount of 2-methyl-2(p-chlorophenyl)-4,5-dichloroindan-1,3,6-triol there is obtained [1,3-dihydroxy-2-methyl-2-(p-chlorophenyl)-4,5-dichloro-6-indanyloxy]acetic acid.

EXAMPLE 8

[1,3-Dihydroxy-2-methyl-2-(2-thienyl)-4,5-dichloro-6-indanyloxy]acetic acid

By the process of Example 2A but substituting for the 4'-chloro-5'-methyl-6'-hydroxyspiro(cyclopentane-1,2'-indan)-1',3'-dione used therein an equivalent amount of 2-methyl-2-(2-thienyl)-4,5-dichloro-6-hydroxyindan-1,3-dione there is obtained 2-methyl-2-(2-thienyl)-4,5-dichloroindan-1,3,6-triol.

By the process of Example 2B but substituting for the 4'-chloro-5'-methylspiro(cyclopentane-1,2'-indan)-1',3',6'-triol an equivalent amount of 2-methyl-2-(2-thienyl)-4,5-dichloroindan-1,3,6-triol there is obtained [1,3-dihydroxy-2-methyl-2-(2-thienyl)-4,5-dichloro-6-indanyloxy]acetic acid.

The novel compounds of this invention are diuretic and saluretic agents. In addition, these compounds are also able to maintain the uric acid concentration in the blood at pretreatment levels or even cause a decrease in uric acid concentration. The compounds of this invention can be administered to patients (both animal and human) in a wide variety of therapeutic dosages in conventional vehicles as, for example, by oral administration in the form of a tablet or by intravenous injection. Also, the daily dosage of the products may be varied over a wide range as, for example, in the form of scored tablets containing 5, 10, 25, 50, 100, 150, 250 and 500 milligrams of the active ingredient for the symptomatic adjustment of the dosage to the patient to be treated. These dosages are well below the toxic or lethal dose of the products.

A suitable unit dosage form of the products of this invention can be administered by mixing 50 milligrams of a [1,3-dihydroxy-2-substituted and 2,2-disubstituted-indanyloxy(or thio)]alkanoic acid (I) or a suitable salt, ester or amide derivative thereof, with 149. mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employed. Compressed tablets, pills, or other desired unit dosages can be prepared to incorporate the compounds of this invention by conventional methods, and if desired, can be made up as elixirs or as injectable solutions by methods well known to pharmacists. An effective amount of the drug is ordinarily supplied at a dosage level of from about 1 mg. to about 50 mg./kg. of body weight. Preferably the range is from about 0.5 mg. to 10 mg./kg. of body weight.

It is also within the scope of this invention to combine two or more of the compounds of this invention in a unit dosage form or to combine one or more of the compounds of this invention with other known diuretics and saluretics or with other desired therapeutic and/or nutritive agents in dosage unit form.

The following example is included to illustrate the preparation of a representative dosage form:

| Dry-filled capsules containing 50 mg. of active ingredient per capsule | |
| --- | --- |
|  | Per Capsule |
| (1,3-Dihydroxy-2-methyl-2-phenyl-4,5-dichloro-6-indanyloxy)acetic acid | 50 mg. |
| Lactose | 149 mg. |
| Magnesium Stearate | 1 mg. |
| Capsule (Size No. 1) | 200 mg. |

The (1,3-dihydroxy-2-methyl-2-phenyl-4,5-dichloro-6-indanyloxy)acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

It will be apparent from the foregoing description that the [1,3-dihydroxy-2-substituted and 2,2-disubstituted indanyloxy(or thio)]alkanoic acids (I) of this invention constituted a valuable class of compounds which have not been prepared heretofore. One skilled in the art will also appreciate that the processes disclosed in the above examples are merely illustrative and are capable of a wide variation and modification without departing from the spirit of this invention.

What is claimed is:

1. A compound of the formula:

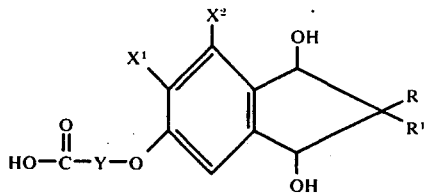

wherein R is lower alkyl having from 1 to 5 carbon atoms, cycloalkyl having from 5 to 6 nuclear carbon atoms, phenyl or substituted phenyl wherein the substituent is lower alkyl or halo; $R^1$ is hydrogen, lower alkyl having 1 to 5 carbon atoms, lower alkenyl having 3 to 5 carbon atoms, lower alkynyl having from 3 to 5 carbon atoms, phenyl lower alkyl wherein lower alkyl has 1 to 3 carbon atoms, or phenyl lower alkenyl wherein the lower alkenyl contains from 2 to 5 carbon atoms, phenyl or substituted phenyl wherein the substituents are lower alkyl or halo; or R and $R^1$ may be joined together with the carbon atoms to which they are attached to form a cycloalkyl having from 3 to 7 nuclear carbon atoms; $X^1$ is hydrogen, methyl or halo, and $X^2$ is methyl or halo; or $X^1$ and $X^2$ may be joined to form a hydrocarbylene chain containing 3 to 4 carbon atoms; and y is alkylene or haloalkylene containing a maximum of 4 carbon atoms, the diastereomeric form, the lower alkyl ester and the non-toxic, pharmacologically acceptable salt derivative thereof.

2. A compound of the formula:

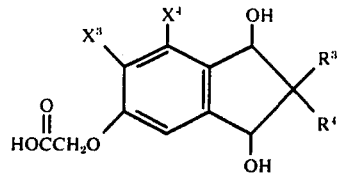

wherein $R^3$ is lower alkyl having from 1 to 3 carbon atoms or cycloalkyl having from 5 to 6 nuclear carbon atoms; $R^4$ is hydrogen, lower alkyl having from 1 to 3 carbon atoms, phenyl, loweralkyl phenyl the lower alkyl having from 1 to 3 carbon atoms, tolyl, halophenyl, chlorophenyl; $R^3$ and $R^4$ may be joined together with the carbon atoms to which they are attached to form a cycloalkyl radical containing from 5 to 6 nuclear carbon atoms; $X^3$ and $X^4$ are the same or different radicals selected from methyl or chloro; the lower alkyl ester and the non-toxic pharmaceutically acceptable salt derivative thereof.

3. A compound according to claim 2 wherein $R^4$ is hydrogen; $R^3$ is ethyl and $X^3$ and $X^4$ are methyl.

4. A compound of the formula:

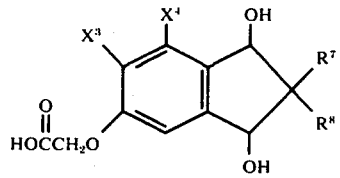

wherein

, $R^7$ is lower alkyl containing from 1 to 3 carbon atoms;

$R^8$ is hydrogen, lower alkyl containing from 1 to 3 carbon atoms, phenyl and p-chlorophenyl;

$X^3$ and $X^4$ are the same or different radicals selected from methyl or chloro, the lower alkyl ester derivative and the non-toxic pharmaceutically aceptable salt derivative thereof.

5. A compound according to claim 2 wherein $R^3$ is methyl; $R^4$ is phenyl and $X^3$ and $X^4$ are methyl.

6. A compound according to claim 2 wherein $R^3$ is methyl; $R^4$ is p-chlorophenyl and $X^3$ and $X^4$ are methyl.

7. A compound according to claim 2 wherein $R^3$ is ethyl; $R^4$ is phenyl and $X^3$ and $X^4$ are chloro.

8. A compound according to claim 2 wherein $R^3$ is methyl; $R^4$ is phenyl and $X^3$ and $X^4$ are chloro.

9. A compound according to claim 2 wherein $R^3$ is methyl; $R^4$ is p-chlorophenyl and $X^3$ and $X^4$ are chloro.

10. A compound according to claim 2 wherein $R^3$ is cyclopentyl and $R^4$ is methyl; $X^4$ is chloro and $X^3$ is methyl.

11. A compound according to claim 2 wherein $R^3$ is methyl; $R^4$ is ethyl, and $X^3$ and $X^4$ are chloro.

12. A compound according to claim 2 wherein $R^3$ and $R^4$ are connected together to form a cyclopentane ring; $X^3$ is chloro and $X^4$ is methyl.

13. A compound according to claim 2 wherein $R^3$ is methyl; $R^4$ is phenyl and $X^3$ is methyl and $X^4$ is chloro.

14. A compound according to claim 2 wherein $R^3$ is methyl; $R^4$ is p-chlorophenyl and $X^3$ is methyl and $X^4$ is chloro.

15. A compound according to claim 2 wherein $R^3$ is cyclopentyl; $R^4$ is methyl; $X^3$ and $X^4$ are chloro.

16. A compound according to claim 2 wherein $R^3$ is isopropyl; $R^4$ is methyl; $X^3$ and $X^4$ are chloro.

* * * * *